United States Patent [19]

Haas et al.

[11] Patent Number: 5,543,538
[45] Date of Patent: Aug. 6, 1996

[54] ACRYLOYLOXYPROPYLALKOXYSILANES, PROCESS FOR THEIR PREPARATION AND USE THEREOF

[75] Inventors: Margret Haas, Koenigswinter; Guenther Bernhardt, St. Augustin, both of Germany

[73] Assignee: Huels Aktiengesellschaft, Marl, Germany

[21] Appl. No.: 521,582

[22] Filed: Aug. 30, 1995

[30] Foreign Application Priority Data

Aug. 30, 1994 [DE] Germany .................. 44 30 729.2

[51] Int. Cl.$^6$ ........................................ C07F 7/08
[52] U.S. Cl. ............................ 556/401; 106/481
[58] Field of Search ...................... 556/401; 106/481

[56] References Cited

U.S. PATENT DOCUMENTS

| | | |
|---|---|---|
| 3,258,477 | 6/1966 | Plueddemann et al. . |
| 4,927,948 | 5/1990 | Bernhardt et al. ............ 556/401 |
| 4,946,977 | 8/1990 | Bernhardt et al. . |
| 5,103,032 | 4/1992 | Turner et al. ............... 556/401 |
| 5,117,027 | 5/1992 | Bernhardt et al. . |

FOREIGN PATENT DOCUMENTS 0324747 12/1990 European Pat. Off. .
0267698 6/1993 European Pat. Off. .

OTHER PUBLICATIONS

Makromolekulare Chemie, vol. 73, pp. 85–108, 1964, Gerd Rossmy, et al., "1,2–Siloxacycloalkane 1. Mitt. Synthese und Polymerisationsverhalten".

Verlag Chemie, pp. 232–234, 1954, Louis F. Fieser, et al., "Lehrbuch der Organischen Chemie".

*Primary Examiner*—Paul F. Shaver
*Attorney, Agent, or Firm*—Oblon, Spivak, McClelland, Maier & Neustadt, P.C.

[57] ABSTRACT

Acryloyloxypropylalkoxysilane compositions containing one or more acryloyloxypropylalkoxysilanes of the formula $$CH_2=\underset{R}{\underset{|}{C}}-COO(CH_2)_3-Si(OR^2)_{3-m},\overset{R^1_m}{\overset{|}{\phantom{C}}}$$

wherein $R^1$ and $R^2$ are, independently, identical or different alkyl groups having 1 to 4 carbon atoms, m is an integer from 0 to 2 and R is hydrogen or a methyl group, and an amount of one or more tertiary amines sufficient to provide a pH higher than the intrinsic pH of the acryloyloxypropylalkoxysilane itself and to improve shelf storage, a process for their preparation, and to their use in preparing silicon-containing coating materials and paints.

14 Claims, No Drawings

ACRYLOYLOXYPROPYLALKOXYSILANES, PROCESS FOR THEIR PREPARATION AND USE THEREOF

BACKGROUND OF THE INVENTION

1. Field of the Invention

The present invention relates to acryloyloxypropylalkoxysilane compositions, to a process for their preparation, and to the use thereof in silicon-containing coating materials and paints.

2. Discussion of the Background

Acryloyloxypropylalkoxysilanes, such as 3-methacryloyloxypropyltrimethoxysilane are important starting materials for the production of silicon-containing coating materials and paints (EP-B 0 324 747 and EP-B 0 267 698). Frequently, the pH of these silanes plays a decisive role in the production and formulation of coating materials and paints and affects the storage properties of the coating materials and paints. Within the industry there is a requirement for acryloyloxypropylalkoxysilanes having a pH of from about 5 to 6.

However, conventional acryloyloxypropylalkoxysilanes, prepared by various processes (see U.S. Pat. Nos. 3,258,477, 4,946,977, 5,117,027), have intrinsic pH values which are only from around 3 to < 5.

Organosilanes are not protonic or Lewis acids in the conventional sense, but in contact with water they cause an acidification of the aqueous phase. The degree of acidification can be determined by measuring the pH by known methods. By definition, the pH measured in water is assigned to the organosilane.

While an increase in the pH of acryloyloxypropylalkoxysilanes by addition of basifying compounds such as alkali metal hydroxides, alkaline earth metal hydroxides, alkali metal alcoholates or alkaline earth metal alcoholates is indeed possible, such mixtures are not stable on storage, and the acrylic ester bond is rapidly cleaved after a short time (G. Rossmy and G. Körner, Makromolekulare Chem. 73 (1964), p. 85–108). The cleavage occurs with particular readiness in the presence of proton-donating solvents such as alcohols or water.

SUMMARY OF THE INVENTION

Accordingly, one object of the present invention is to provide acryloyloxypropylalkoxysilane compositions which have a pH higher than the intrinsic pH of the acryloyloxypropylalkoxysilane contained therein, and are stable on storage.

A further object of the present invention is to provide a process for the preparation of such acryloyloxypropylalkoxysilane compositions.

A further object of the present invention is to provide coating materials and paints containing such compositions.

These and other objects of the present invention have been satisfied by the discovery of acryloyloxypropylalkoxysilane compositions containing one or more tertiary amines, which compositions have a pH higher than the intrinsic pH of the silane itself and are outstandingly stable on storage. In this case, rapid cleavage of the acrylic ester bond does not take place, even in the presence of proton-donating solvents. Moreover, the color specification required by the coatings and paint industry is met outstandingly by the compositions according to the invention.

DETAILED DESCRIPTION OF THE PREFERRED EMBODIMENTS

The present invention relates to compositions comprising acryloyloxypropylalkoxysilanes of the formula

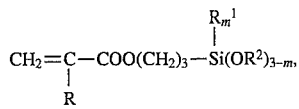

in which $R^1$ and $R^2$ are identical or different alkyl groups having 1 to 4 carbon atoms, m is an integer of from 0 to 2 and R is hydrogen or a methyl group, and one or more tertiary amines.

Preferably, tertiary amines having a $pK_b$ of between 3 and 5 are used. The definition of the $pK_b$ value can be found, inter alia, in "Lehrbuch der Organischen Chemie" (Textbook of Organic Chemistry) (1954), page 233, L. F. Fieser and M. Fieser. In addition, the compositions according to the present invention have a pH which is from > 3 to < 7, preferably from $\geq$ 5 to < 7, and most preferably from $\geq$ 5 to $\leq$ 6.

Among the acryloyloxypropylalkoxysilanes used in the compositions according to the present invention, the most preferred compound is 3-methacryloyloxypropyltrimethoxysilane. The acryloyloxypropylalkoxysilanes of the present composition may be used singularly or in combinations of two or more.

The present invention also relates to a process for the preparation of storage stable acryloyloxypropylalkoxysilane compositions of the present invention, comprising adding an amount of one or more tertiary amines to the acryloyloxypropylalkoxysilanes, the amount being sufficient to adjust the pH to the desired range and provide increased storage stabiliy.

The pH of the present compositions is established by addition of at least one tertiary amine to give a pH from > 3 to < 7, preferably from $\geq$ 5 to < 7 and, most preferably, from $\geq$ 5 to $\leq$ 6. The desired pH of the final composition is established at a point higher than the intrinsic pH of the respective acryloyloxypropylalkoxysilane, such that at least one tertiary amine is added with stirring. It is preferred to add to the acryloyloxypropylalkoxysilanes at least one tertiary amine in a quantity of from 10 to 500 ppm by weight.

The preferred tertiary amines to be used in the present compositions are those having a $pK_b$ of between 3 and 5. The tertiary amines can be used singularly or in combinations of two or more.

Unlike primary or secondary amines, in an essentially anhydrous mixture tertiary amines do not react with the double bonds of acryloyloxypropylalkoxysilanes. The tertiary amines of the present invention can be tertiary mono-, di- or triamines.

Examples of tertiary monoamines suitable for use in the present invention include:

triethylamine, tripropylamine, tributylamine, trioctylamine, diethyloctylamine, triisobutylamine, tri-2-ethylhexylamine, N,N-dimethylethylamine, N,N-dimethylisopropylamine, N,N-dimethylisobutylamine, N,N-dimethyl-2-ethylhexylamine,
N-methylditridecylamine, and dimethylcyclohexylamine.

Examples of tertiary diamines suitable for use in the present invention are:

bisdimethylaminomethane, N,N,N',N'-tetramethylethylenediamine and N,N,N'N'-tetramethyl-1,3-diaminopropane.

An example of a tertiary triamine suitable for use in the present invention is:

N,N,N',N'',N''-pentamethyldiethylenetriamine

The present invention also relates to silicon-containing coating materials and paints which comprise the acryloyloxypropylalkoxysilane compositions of the present invention and/or polymers thereof and/or copolymers thereof. These coating materials and paints can be prepared using conventional methods for preparation of silicon-containing coating materials and paints, with the silicon compound being the acryloyloxypropylalkoxysilane compositions of the present invention. The compositions of the present invention are used in the same amounts as conventional acryloyloxypropylalkoxysilanes, which do not contain the tertiary amines required in the present compositions.

Table I shows the pH of 3-methacryloyloxypropyltrimethoxysilane and the pH following addition of different quantities of tributylamine; thus illustrating, by example, an outstanding mode of action of the present invention. A further advantage of the present invention is that within the pH range between 4.4 and 6.2 for the most preferred silane, there is practically a linear correlation between the change in pH and the quantity of tertiary amines added to the acryloyloxypropylalkoxysilane. It is therefore a simple matter to estimate beforehand, the quantity of tertiary amines needed to obtain a specific pH.

Having generally described this invention, a further understanding can be obtained by reference to certain specific examples which are provided herein for purposes of illustration only and are not intended to be limiting unless otherwise specified.

EXAMPLES

Example 1 a) Determination of the pH of commercial 3-methacryloyloxypropyltrimethoxysilane:

Two parts by weight of DYNASYLAN MEMO-E (commercial product from Hüls AG) were added all at once to three parts by weight of double-distilled water, while stirring with a magnetic stirrer, and the constituents were intimately mixed at room temperature for 10 minutes. After switching off the stirrer and leaving the mixture to stand for 30 minutes, the pH of the upper, aqueous phase was determined by means of a single-rod pH measuring cell (type: N 1042 A with integrated temperature sensor Pt 100 from Schott) and pH-meter (type: microprocessor pH meter CG 832 from Schott). The measured pH was 4.4.

b) Determination of the pH as a function of the amine concentration:

Defined quantities of tributylamine ("purum" from Fluka, purity > 98% (GC)) were weighed into commercial 3-methacryloyloxypropyltrimethoxysilane (DYNASYLAN MEMO-E) and the pH was determined as specified above. The results are summarized in Table 1.

TABLE 1 pH of 3-methacryloyloxypropyltrimethoxysilane before and after addition of different quantities of tributylamine 3-methacryloyloxypropyltrimethoxysilane

| Tributylamine content [ppm by weight] | pH |
|---|---|
| 0 | 4.4 |
| 25 | 4.6 |
| 50 | 4.7 |

TABLE 1-continued pH of 3-methacryloyloxypropyltrimethoxysilane before and after addition of different quantities of tributylamine 3-methacryloyloxypropyltrimethoxysilane

| Tributylamine content [ppm by weight] | pH |
|---|---|
| 75 | 4.8 |
| 100 | 5.0 |
| 150 | 5.3 |
| 200 | 5.6 |
| 300 | 6.2 |
| 400 | 6.5 |

For all established pH values, the 3-methacryloyl-oxypropyltrimethoxysilane according to the invention provided a storage stability of more than 6 months.

Example 2

Example 1 was repeated using, instead of 3-methacryloyloxypropyltrimethoxysilane, the compound 3-acryloyloxypropyltriethoxysilane having an intrinsic pH of 4.8 and, instead of tributylamine, the compound diethyloctylamine. Following addition of 179 ppm by weight of diethyloctylamine, a pH of 5.8 was found.

For all established pH values, the composition of the present invention containing 3-acryloyloxypropyltriethoxysilane likewise gave a storage stability of more than 6 months.

Example 3

Example 1 was repeated but using, instead of 3-methacryloyloxypropyltrimethoxysilane, the compound 3-methacryloyloxypropylmethyldimethoxysilane having an intrinsic pH of 4.5. Following the addition of 249 ppm by weight of tributylamine, a pH of 6.0 was measured.

Here too, the storage stability of the composition containing 3-methacryloyloxypropylmethyldimethoxysilane according to the present invention was more than 6 months.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An acryloyloxypropylalkoxysilane composition comprising one or more acryloyloxypropylalkoxysilanes of the formula:

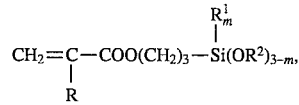

wherein $R^1$ and $R^2$ are, independently, identical of different alkyl groups having 1 to 4 carbon atoms, m is an integer from 0 to 2 and R is hydrogen or a methyl group; and an amount of one or more tertiary amines sufficient to raise the pH of the composition to a value higher than the pH of said acryloyloxypropylalkoxysilanes, and wherein said one or more tertiary amines is selected from the group consisting of tertiary mono-, di-, and triamines containing only alkyl or cycloalkyl substituents.

2. The composition according to claim 1, wherein the acryloyloxypropylalkoxysilane is 3-methacryloyloxypropyltrimethoxysilane.

3. The composition according to claim 1, wherein the composition has a pH of from > 3 to < 7.

4. The composition according to claim 3, wherein the composition has a pH of from ≧ 5 to < 7.

5. The composition according to claim 4, wherein the composition has a pH of from ≧ 5 to ≦ 6.

6. The composition according to claim 1, wherein said one or more tertiary amines have a p$K_b$ of from 3 to 5.

7. The composition according to claim 1, wherein said one or more tertiary amines are present in a total amount of from 10 to 500 ppm by weight, based on the total weight of the composition.

8. A process for the preparation of storage stable acryloyloxypropylalkoxysilane compositions, comprising adding to a composition of one or more acryloyloxypropylalkoxysilanes of the formula

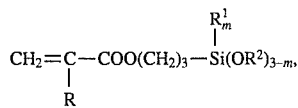

wherein $R^1$ and $R^2$ are, independently, identical or different alkyl groups having 1 to 4 carbon atoms, m is an integer from 0 to 2 and R is hydrogen or a methyl group; and an amount of one or more tertiary amines sufficient to raise the pH of the composition to a value higher than the pH of said acryloyloxypropylalkoxysilanes, and wherein said one or more tertiary amines is selected from the group consisting of tertiary mono-, di-, and triamines containing only alkyl or cycloalkyl substituents.

9. The process according to claim 8, wherein the amount of said one or more tertiary amines added is sufficient to provide a pH of the composition of from > 3 to < 7.

10. The process according to claim 9, wherein the amount of said one or more tertiary amines added is sufficient to provide a pH of the composition of from ≧ 5 to < 7.

11. The process according to claim 10, wherein the amount of said one or more tertiary amines added is sufficient to provide a pH of the composition of from ≧ 5 to ≦ 6.

12. The process according to claim 8, wherein said one or more tertiary amines has a p$K_b$ of between 3 and 5.

13. The process according to claim 8, wherein the amount of said one or more tertiary amines added is from 10 to 500 ppm by weight.

14. Silicon-containing coating materials and paints prepared by combining an acryloyloxypropylalkoxysilane composition according to claim 1, a polymer thereof, a copolymer thereof, or a combination thereof, with a conventional coating material or paint composition.

* * * * *